United States Patent [19]

Orlando

[11] Patent Number: 4,653,335
[45] Date of Patent: Mar. 31, 1987

[54] SAMPLING SYSTEM FOR GRINDING MILLS

[75] Inventor: John J. Orlando, Rivervale, N.J.

[73] Assignee: Inco Alloys International, Inc., Huntington, W. Va.

[21] Appl. No.: 712,569

[22] Filed: Mar. 15, 1985

[51] Int. Cl.[4] .......................... G01N 1/20; G01N 1/10
[52] U.S. Cl. .............................. 73/863.85; 73/863.86; 73/863.42; 73/863.23
[58] Field of Search ........... 73/863.85, 863.86, 863.82, 73/863.21, 863.23, 863.25, 863.42

[56] References Cited

U.S. PATENT DOCUMENTS

| | | | |
|---|---|---|---|
| 3,229,711 | 1/1966 | Leopold, Jr. et al. | 73/863.85 X |
| 3,528,294 | 9/1970 | Manevy | 73/863.42 |
| 3,613,453 | 10/1971 | Small et al. | 73/863.86 X |
| 3,740,210 | 6/1973 | Bomford et al. | 75/0.5 AC |
| 3,747,411 | 7/1973 | McDermott et al. | 73/863.86 X |
| 4,096,754 | 6/1978 | Beveridge, Jr. et al. | 73/863.85 X |
| 4,262,354 | 4/1981 | Morrison | 73/863.86 |
| 4,294,181 | 10/1981 | Kalwaitis | 73/863.85 |
| 4,346,611 | 8/1982 | Welker | 73/863.86 |
| 4,354,392 | 10/1982 | Goodell et al. | 73/863.86 |
| 4,481,833 | 11/1984 | Bajek | 73/863.21 |

OTHER PUBLICATIONS

Strahman Sampling Valve Publication; 2 pages, by Aug. 1960.
"Probe Design for Mill Fire Detection by Carbon Monoxide Monitoring"; CEGB Technical Disclosure Bulletin; No. 274, pp. 1–10, Jan. 1977; W. I. McConachie.
Catalog B–5 of Paul O. Abbe Inc., entitled Ball & Pebble Mills; 24 pages; by Jul. 1985.

Primary Examiner—Stewart J. Levy
Assistant Examiner—Tom Noland
Attorney, Agent, or Firm—Miriam W. Leff; Raymond J. Kenny

[57] ABSTRACT

A system for obtaining a sample of particulate material being processed under seal from the air in a batch-type rotary grinding mill which permits sampling of material being processed without disturbing the seal. The system is comprised of a sampling member and a plug member which can be interchanged under seal while maintaining the seal in the mill.

17 Claims, 3 Drawing Figures

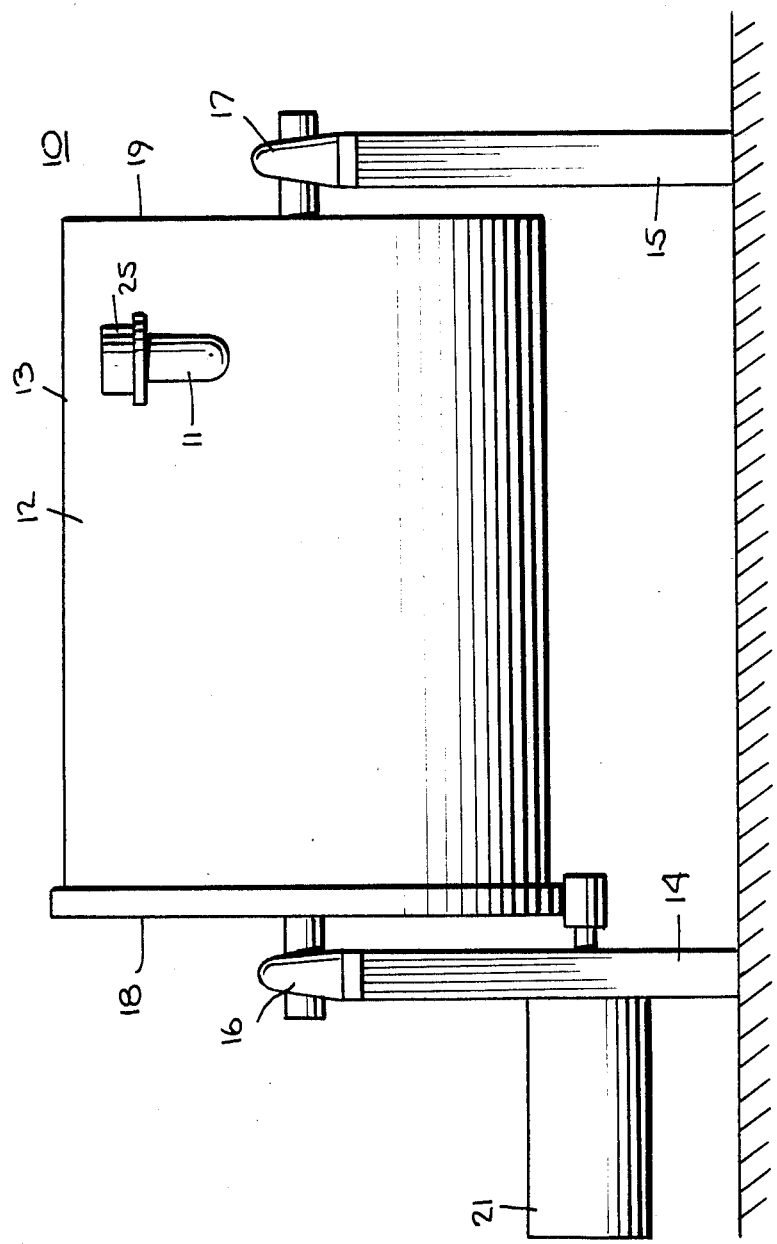

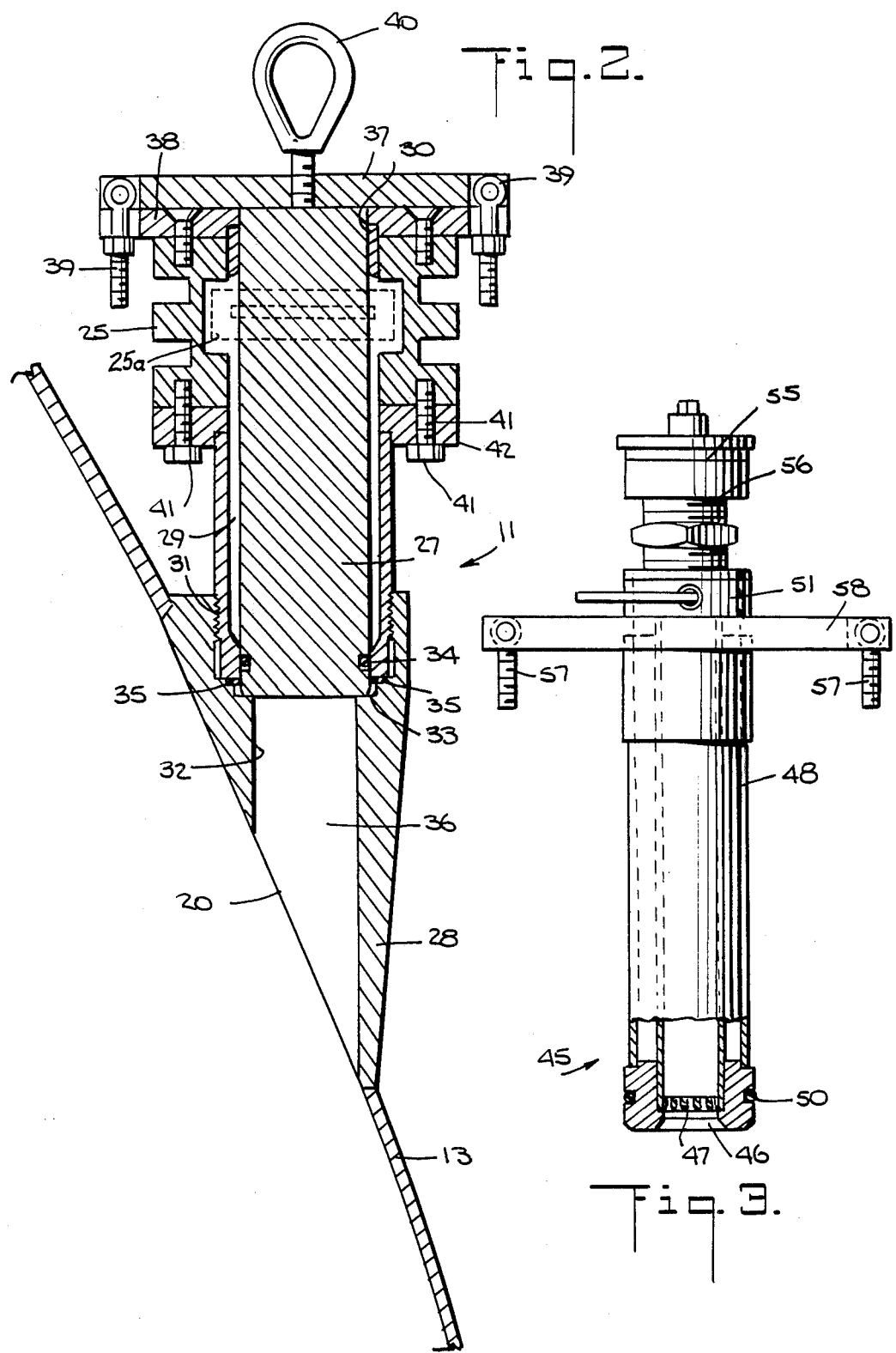

SAMPLING SYSTEM FOR GRINDING MILLS

FIELD OF INVENTION

The invention relates to a sampling system for materials being processed under sealed conditions in a grinding mill. More particularly, it relates to a system for sampling powder being processed in a batch-type, rotary, grinding mill operated under seal to the air.

BACKGROUND OF INVENTION

In milling certain types of powders it is often necessary or desirable to have a positive control of the atmosphere within the mill at all times. For example, readily oxidizable materials such as aluminum, titanium, magnesium, lithium and fine powders of many compositions are combustible or even explosive under certain conditions or they may be contaminated by the presence of air. In milling such materials the control of the atmosphere must extend to charging and discharging of the mill without opening the mill to air. The problem of exposure to air during operation of the mill, charging materials to the mill and unloading the mill, extends to sampling of powders in the mill, e.g. to determine the current state of the processing.

The present invention is not restricted to the processing of any particular powders or any particular grinding mill. It is especially useful, however, for sampling powders which must be processed in an airtight system and in a batch-type rotary mill. For that reason it is described below with reference to metal powders which are readily oxidized and are processed to obtain dispersion strengthened materials or alloys by powder metallurgy routes. Of necessity the milling of such materials must be carried out in a controlled atmosphere, e.g., sealed to air.

The problem encountered in milling powders are particularly troublesome in the mechanical alloying of readily oxidizable metals such as aluminum, magnesium and lithium. Mechanical alloying has been described in detail in the literature in patents. U.S. Pat. No. 3,740,210, U.S. Pat. No. 3,816,080 and U.S. Pat. No. 3,837,930, for example, involve the mechanical alloying of aluminum alloys and other composite materials containing aluminum. In the practice of mechanical alloying the components of the product are charged in powder form into a high energy milling device such as a ball mill where, in an environment free of or reduced in amount of free or combined oxygen, the powders which are dry or substantially dry are ground down to a very fine size initially, prior to particle agglomeration in the latter stages of the process. This initial grinding increases the total surface area of the metallic powders significantly. Since any freshly exposed surface of the powder is not oxidized, it is very hungry for oxygen to the extent that the powders in this condition will burn and/or might explode spontaneously if exposed to air. Thus, any port in the mill, for example, for charge, discharge or sampling of powders, is a source of potential danger from the standpoint of the quality of the product produced and the possibility of a fire and/or an explosion. To avoid the hazards of exposure to air, any discharge of material must be effected while maintaining a positive control of the environment in the mill, and in the discharge and/or sampling system.

It has been known to operate a rotary ball mill with a plug in an opening in the shell, the plug being replaceable with a grate during discharge. For protection of the environment during discharge the shell is enclosed in a housing. When the milling cycle is finished the housing is opened to replace the plug with a grate, then the housing is closed for the discharge cycle. During the discharge cycle the discharge opening is rotated to the underside of the shell, thereby permitting the powder to run out into the housing. The rotation for discharge of material can be repeated. This arrangement is not satisfactory. It opens the system to the atmosphere when the plug is replaced by the grate. Powder discharged from the shell tends to accumulate in the housing, thereby requiring cleaning out of the housing after each run and further opening the system to air. Opening of the housing is a source of contamination of the powder discharged from the mill and to subsequent runs in the mill. A further serious problem is that when the shell rotates inside the housing the discharging powder may be in the explosion range in terms of concentration of various portions of powder discharged in any cycle. Another proposed method for discharge is by gas sweep through the mill to pick up particles and carry them to a classification system. This involves the use of a combination of devices such as dropout chambers, cyclones, bag filters, blowers and the like. Since the powder conveyed is combustible and/or explosive, this gas sweep system poses a significant hazard. Furthermore, it is difficult to seal against infiltration of air and against leaks.

The conventional discharge devices are designed to discharge large amounts of powder from the mill. However, it is often highly desirable to check the progress of powder in the mill by obtaining just small samples. The same problems of contamination, burning and explosions apply to obtaining small samples as they do to discharging the mill. It is necessary to obtain samples of powders from the mill without exposing the mill contents or the samples to air. The present invention is directed to obtaining samples from grinding mills without exposing the mill contents or the samples to air. It is an advantage of the present system that it can be incorporated into existing mills.

In co-pending U.S. patent application Ser. No. 712,570 filed of even date herewith a system for charging a ball mill under seal is disclosed. The present invention, while not limited to the disclosed system, can be readily adapted for use with it.

STATEMENT OF THE INVENTION

In accordance with the present invention a batch-type mill for grinding material to a particulate form, e.g. a powder, under seal to the environment is provided with a system for obtaining a sample of material being processed in the mill without disturbing the seal in the mill and, if desired, without exposing the sample to the atmosphere, said system comprising:

I. a hollow rotatably mounted shell, said shell having a peripheral wall, means for rotating the shell and grinding media within the shell;

II. at least one sampling orifice located in the wall of the shell for outward discharge from the shell of material processed in the shell, said orifice being sealable to the atmosphere; and III. at least one sampling assembly for receipt of the sample from the shell, said sampling assembly comprising:
 (A) a sampling chamber sealably secured on the shell over each sampling orifice in the shell, said chamber having an inner wall forming a longitudinal channel with ports at either end, one port being aligned with the sampling orifice in the shell;

(b) a removable hollow sampling member sealably insertable and retaining in the sampling chamber and comprising a tubular portion at one end of the sampling member for insertion into the sampling chamber and a sealable collection chamber at the opposite end, the tubular portion having a port of entry for the sample, means to seal the collection chamber, and means for maintaining the sampling member in sealed relationship with respect to the atmosphere;

(C) grinding media blocking means to prevent the grinding media from outward passage from the shell into the sampling member;

(D) removable blocking means for preventing, in the absence of the removable sampling member, the outward passage of material from the shell through the central channel of the sampling chamber;

(E) means for maintaining the removable blocking means and removable sampling member in a sealed relationship with the sampling chamber;

(F) valve means for sealing the sampling chamber from the atmosphere in the absence of the removable sampling member and removable blocking means; and (G) sealing means for interchanging the sampling member and removable blocking means without exposing the material in the shell to the atmosphere.

The removable blocking means may be a plug member which is slidably insertable in the sampling chamber and can be maintained in sampling chamber in a sealable relationship in respect to the air. The grinding media may be, e.g., balls, pebbles, rods. The means for blocking passage of the grinding media outwardly from the shell may be, for example, a grate, sieve, screen or the like (referred to herein as a grate) across the port at the entry end of the sampling member.

The sampling chamber valve means, e.g. comprising a slide, gate, ball or other appropriate valve is incorporated in the sampling chamber to prevent exposure of the mill contents and sample from the air when the sampling member and/or blocking means (e.g., a plug member) do not serve this purpose. In this way neither the contents of the mill nor the sample in the chamber or in the sampling member will be exposed to the atmosphere. Valves and other closure devices may be used in the sampling member and plug member. To obtain a sample the plug member is replaced by the sampling member while the mill is closed to the atmosphere by the sampling chamber valve, and the sampling chamber is positioned above the contents of the mill. When the sampling member is in place and sealed to the atmosphere the sampling chamber valve may be opened, and the mill rotated. A sample will flow from the mill into the sampling member, while the balls are retained in the mill.

In one advantageous embodiment of the present invention the sampling system is incorporated in a batch-type mill which is capable of operating under a controlled environment, and the sampling member is part of a combined system designed for charging material to the shell as well as sampling material under seal to the atmosphere. That is, the combined system comprises the loading and sampling assemblies. The sampling assembly, as described above, comprises a removable sealable plug member for insertion into the sampling chamber in a sealed relationship with the sampling chamber relative to the atmosphere; a removable, sealable sampling member for insertion into the sampling chamber in a sealed relationship therewith relative to the atmosphere, and valve means associated with the sampling chamber for interchanging the removable plug member and removable sampling member without breaking the seal in the sampling chamber with respect to the atmosphere. For loading the mill a charging means is inserted in the sampling chamber. A suitable charging means is described in the aforementioned copending patent application. In this combined embodiment the sampling chamber and plug member also serve as a part of the system for charging the mill.

In a preferred embodiment of this invention a portion of the sampling chamber is provided with a retaining section outwardly located in respect to the valve means in the chamber for maintaining the plug member or sampling member in sealed relationship with the chamber while the valve means for the sampling chamber is in open position for interchange of the plug member and sampling member. The sealable sampling member may be equipped with a valve for maintaining the sample of material in a protective atmosphere when the sampling member is removed from the mill.

The material processed in the mill may comprise elements, compounds, mixtures, alloys, ceramics and combinations thereof. Examples of elements which may be present in major or minor amounts are nickel, copper, zinc, titanium, zirconium, niobium, molybdenum, vanadium, tin, aluminum, silicon, chromium, lanthanum; examples of compounds are oxides, nitrides and/or carbides of aluminum, magnesium, yttrium, silicon, cerium and lanthanum; examples of alloys are master alloys of aluminum-lithium and aluminum-magnesium. The present invention is particularly useful when the material to be processed must be charged to and/or processed in a mill under a controlled atmosphere. The present invention is particularly advantageous for processing in a ball mill metal powders which are readily oxidized and are prepared as dispersion strengthened materials or alloys by powder metallurgy routes. Of necessity the milling of such materials must be carried out in a controlled atmosphere, e.g. hermetically sealed or in a purgative atmosphere, or in an environment of controlled gas or gas flow. However, it will be understood that the present invention is, generally, especially useful for processing in a mill any materials where a controlled atmosphere is required or beneficial. Thus, for example, the present invention can be used advantageously for preparing by a powder metallurgy route dispersion strengthened alloys having, e.g., nickel, copper, iron, titanium, magnesium, chromium or aluminum as a major constituent.

BRIEF DESCRIPTION OF THE DRAWING

A further understanding of the objects and advantages of the invention will become apparent from the following description taken in conjunction with the accompanying drawing in which:

FIG. 1 is a schematic diagram of a rotary mill showing a sampling chamber in accordance with an embodiment of the present invention.

FIG. 2 is a detail of the sampling assembly with a sealing plug member in place in the assembly.

FIG. 3 shows a sampling member, which is inserted in the sampling chamber in place of the plug member in order to obtain a sample of powder from the mill.

DESCRIPTION OF A PREFERRED EMBODIMENT

Referring to the drawing, FIG. 1 shows a ball mill 10 with a sampling chamber 11 located on cylindrical shell 12 of the mill. The mill comprises a pair of support members 14 and 15 and a shell 12 mounted on a horizontal axis to rotate on trunnion bearings 16 and 17. The shell 12 comprises a peripheral wall 13, ends 18 and 19 and an orifice 20 (covered by sampling chamber 11) in the wall. A valve, e.g. a slide valve (not shown) in valve housing 25 on chamber 11 can seal the orifice 20 and chamber 11 from the atmosphere. The shell is rotated by drive means 21. When the sampling chamber 11 is in a vertical position it is located at the side of the mill, as shown in FIG. 1. In FIG. 2 a plug member 27 is disposed in the sampling chamber 11. The grinding media, e.g. balls, in the shell, and means to completely discharge the mill are not shown. Only part of the charging system is shown in that the sampling chamber and plug member can also serve as a part of the charging system. Details in FIGS. 2 and 3 comprise the sampling system. Means for discharge of material from the mill other than by means of the sampling system are not shown. It will be understood that other discharge devices can be incorporated in the mill. Appropriate discharge systems are disclosed in co-pending U.S. patent applications Ser. Nos. 712,703 and 712,704, to be U.S. Pat. No. 4,603,814, filed simultaneously herewith.

FIG. 2 shows the sampling chamber 11 sealably mounted on shell wall 13 over orifice 20. Incorporated with the sampling chamber is a valve housing 25 for a sampling chamber valve (S.C. valve) 25a, e.g. a slide or ball valve and an upper sealing tube 30. Removable plug member 27 is slidably disposed in the sampling chamber. The sampling chamber has a shell adapter end 28 which covers orifice 20 and a central inner tubular portion 29. The outer configuration of the shell adapter is frusto-conical. When plug member 27 is removed from the chamber, the S.C. valve (not shown) can seal the sampling chamber from the atmosphere. The S.C. valve is provided to enable sealing of the sampling chamber and shell from the atmosphere when installing and removing the plug member or sampling member 45 shown in FIG. 3. Generally for convenience in assembly, and to allow replacement of sealing gasket 35, the sampling chamber is constructed of separate members which are sealably connected by threaded engagement at juncture 31. The inner wall 32 of the frustum-shaped portion of the sampling chamber has a recess 33 which serves as a seat for the interchangeable insertable members of the sampling assembly. "O" ring 34 and sealing gasket 35 serve to seal the plug member and sampling chamber relative to the atmosphere. Additional sealing means is provided by upper sealing tube 30. Closure cap 37 secured on flange 38 of the upper sealing tube with swing bolts 39 retains the plug member in place during operation of the mill. A lifting means 40 is provided to retract the plug member. The valve housing 25 is secured to the sampling chamber by bolts 41 in flange 42.

In FIG. 3 sampling member 45 comprises tubular portion 48, sampling member valve 51 and collection chamber 56 for samples. The tubular portion 48 is sized to slide into inner channel 29 in the sampling chamber 11 and also to replace the plug member 27 during the sampling mode. Sampling member 45 has an entry end 46 for receiving samples of material from the mill. Across the entry end 46 is grate 47 with openings sized to prevent the grinding media, e.g. balls (not shown), from entering the sampling member 45. "O" ring 50 on sampling member 44 and sealing gasket 35 prevent the sample material, e.g. metal powder, from entering above the recess 33 in the sampling chamber 11. The upper sealing tube 30 (FIG. 2) provides a means to retain plug member 27 and sampling member 45, respectively, in sealable relationship with the sampling chamber during the time they are interchanged with each other. Removable cap 55 is provided on sampling member 45. Between cap 55 and valve 51 is a collecting chamber 56 in which samples can be collected in a protected atmosphere. Valve 51, e.g. a butterfly or other valve, enables the sealing of the sample in the collecting chamber 56 when sampling member 45 is removed from the mill.

To operate the sampling assembly in the mill; shell 12 is rotated so that the sampling chamber 11 is above the ball and mill charge material (as shown in FIG. 1). During operation of the mill the plug member is in position in the sampling chamber (as shown in FIG. 2). Swing bolts 39 are loosened and plug member 27 is retracted to a position just above the S.C. valve so that "O"-ring 34 is in contact with upper sealing tube 30. After the S.C. valve is closed (to seal the sampling chamber) and plug member 27 is removed, sampling member 45 replaces the plug member so that "O"-ring 50 of the sampling member seals with upper sealing tube 30. The S.C. valve is then opened and the sampling member (with valve 51 closed or open) is inserted completely in the sampling chamber 11 with its entry end 46 sealed in recess 33 of the sampling chamber by sealing gasket 35. The sampling member 45 is secured to the sampling chamber 11 with swing bolts 57. Valve 51 in the sampling member is opened and the shell rotated so that the sampling chamber 11 is at the bottom under the mill charge. The sample, e.g. metal powder being processed in the mill, will now fall by gravity from the shell via orifice 20, through the grate 47 and into the collecting chamber 56 at the bottom of the sampling member 45. The grinding media is excluded by grate 47. Subsequent to collection of the sample and while the sampling member 45 is in the inverted position (at the bottom of the mill) valve 51 is closed. The sample is now trapped and sealed in collection chamber 56 formed between valve 51 and removable sampling member cap 55. The shell is now rotated to the starting position, i.e. with the sampling chamber above charge and above the orifice in the shell. Excess material between sampling member valve 51 and grate 47 will fall back and can pass into the shell through orifice 20 in the shell. The sampling member 45 is removed and plug member 27 replaces it by reversing the sequence described above. The sample can be removed from the sampling member by removing cap 55. This can be done in a glove box if continued handling in a protective atmosphere is desired.

The grate can be made removable—and when removed the grinding media can be collected, if desired.

In one embodiment of the invention sampling assembly parts can also serve as part of the charging assembly disclosed in the aforementioned application for removal and substitution of a charging means. However, the sampling assembly is not limited to use in the charging assembly.

In one embodiment of this invention the sampling member contains an inner tube to provide a smooth straight inside surface. Powder in excess of samples in collection chamber will be more easily fall out into the shell. If the smooth passage inner tube is omitted sloped surfaces at the top and bottom of the inner channel of the sampling member can be provided to insure easy removal of excess material from the sampling member.

The mill shell may be, for example, cylindrical, spherical, double or single conical, multi-flat sided, etc. The exact shape of the mill shell is not critical to the invention. Mills may also be double walled (or jacketed) for mill shell cooling. Water or other cooling media may be passed through this space (or jacket). Many varieties of mills and mill adaptations may be used, but it will be appreciated that these adornments are not a factor in this invention. It is understood that appropriate devices can be incorporated in the mill to provide the desired processing environment.

In the embodiment shown in the drawing the mill shell is rotated about an essentially horizontal central axis. In another embodiment of the invention the charging system is adapted for placement on a mill with the drum operated to rotate about a non-horizontal axis.

In an alternative embodiment the sampling member is designed sufficiently long to extend into the shell containing the material being processed and the ball charge. In this way a sample can be extracted from the interior of the shell and/or from a continuum of points along an extended sampling tube.

Although the present invention has been described in conjunction with preferred embodiments, it is to be understood that modifications and variations may be resorted to without departing from the spirit and scope of the invention, as those skilled in the art will readily understand. Such modifications and variations are considered to be within the purview and scope of the invention and appended claims.

The embodiments of the invention in which an exclusive property or privilege is claimed are defined as follows:

1. A system for obtaining a sample of particulate material from a batch-type grinding mill, said material being processed in the mill under seal to the atmosphere, without disturbing the seal, said system comprising:
   I. a hollow rotatably mounted shell, said shell having a peripheral wall, means for rotating the shell and grinding media within the shell;
   II. at least one sampling orifice located in the peripheral wall of the shell for outward discharge from the shell of material processed in the shell, each said orifice being sealable to the atmosphere; and
   III. at least one sampling assembly for receipt of the sample from the shell, each said sampling assembly comprising:
   (A) a sampling chamber sealably secured on the shell over one of said sampling orifices in the shell, said chamber having an inner wall forming a longitudinal channel with ports at either end, one port being aligned with said one sampling orifice in the shell;
   (B) a removable hollow sampling member sealably insertable and retainable in the sampling chamber and comprising a tubular portion at one end of the sampling member for insertion into the sampling chamber and a sealable collection chamber at the opposite end, the tubular portion having a port of entry for the sample, means for sealing the collection chamber, both with respect to the rest of the interior of the sampling member and with respect to the atmosphere;
   (C) grinding media blocking means to prevent the grinding media from outward passage from the shell into the sampling member;
   (D) removable blocking means for preventing, in the absence of the removable sampling member, the outward passage of material from the shell through the central channel of the sampling chamber;
   (E) combination valve and sealing means between the sampling chamber and blocking means or between the sampling chamber and sampling member for maintaining the removable blocking means or removable sampling member in a sealed relationship with the sampling chamber depending on which of the two has been inserted therein;
   (F) said combination valve and sealing means also allowing for sealing the sampling chamber from the atmosphere in the absence of the removable sampling member and removable blocking means; and
   (G) said combination valve and sealing means also allowing for interchanging the sampling member and removable blocking means without exposing the material in the shell to the atmosphere.

2. A system according to claim 1, wherein the removable blocking means used in the absence of the sampling member is a plug member.

3. A system according to claim 2, wherein the inner wall of the sampling chamber contains a recess and wherein said recess serves as a seat for the plug member when said plug member is disposed in the sampling chamber.

4. A system according to claim 2, wherein said combination valve and sealing means comprises a sealing tube located behind a valve means for sealing the sampling chamber relative to the peripheral wall of the shell, hereinafter called "the sampling chamber valve means", said sealing tube and the sampling chamber valve means allowing the interchange to take place without exposure to the atmosphere.

5. A system according to claim 4, wherein seals between the sampling chamber and the plug member or between the sampling chamber and sampling member prevent particulate material from passing into the sampling chamber between the inner wall of the sampling chamber and the plug or sampling member, respectively.

6. A system according to claim 5, wherein the sample of particulate material is a powder and the sample is obtained by a method comprising:
   a. operating the mill to process a mill charge with the removable plug member in position in the sampling chamber until the sampling mode is desired and discontinuing rotation of the mill when the sampling member is above the mill charge;
   b. retracting the plug member to a sealed position in the upper sealing tube above the sampling chamber valve means, thereby sealing the sampling chamber relative to the atmosphere;
   c. closing the sampling chamber valve means;
   d. replacing the plug means with the removable sampling member in sealed position in the upper sealing tube;

e. opening the sampling chamber valve means;
f. securing the sampling member fully in the sampling chamber;
g. rotating the shell so that the sampling member is under the mill charge, thereby permitting a sample of the powder to pass into the sealable collection chamber of the sampling member; and thereafter closing the sampling chamber valve means;
h. rotating the sampling member to a position above the mill charge;
i. retracting the sampling member to a sealed position in the upper sealing tube above the sampling chamber valve means; thereby sealing the sampling chamber relative to the atmosphere;
j. closing the sampling chamber valve means and sealing the sampling chamber; and
k. replacing the sampling member containing the sample with the plug means.

7. A system according to claim 6, wherein the mill charge is a particulate material comprised of at least one of the elements nickel, copper, zinc, titanium, zirconium, niobium, carbon, silicon, molybdenum, vanadium, tin, aluminum, chromium, magnesium, lithium, iron, yttrium and rare earth metals.

8. A system according to claim 7, wherein the processing in the mill is carried out to produce a dispersion strengthened mechanically alloyed product.

9. A system according to claim 8, wherein the mill charge comprises at least one of the elements selected from the group nickel, copper, iron, titanium, magnesium, chromium and aluminum as a major constituent.

10. A system according to claim 7, wherein the mill charge is comprised of aluminum and the processing in the mill is carried out to produce a dispersion strengthened mechanically alloyed product.

11. A system according to claim 1, wherein the means for sealing the collection chamber comprises a valve.

12. A system according to claim 1, wherein the sampling orifice and the sampling chamber covering said orifice are disposed on the peripheral wall so as to be in the vertical position when located at the side of the mill.

13. A system according to claim 1, wherein the grinding mill has a loading means and the sampling chamber and plug member serve dual purposes as part of the loading means as well as part of the sampling assembly.

14. A system according to claim 1, wherein the grinding media blocking means comprises a grate across the entry end of the sampling member.

15. A system according to claim 1, wherein the grinding media blocking means prevents balls from entering the entry port of the sampling member and comprises a grate across the said entry part.

16. A system according to claim 1, wherein the grinding media comprise balls.

17. A system according to claim 1, wherein the inner wall of the sampling chamber contains a recess and wherein said recess serves as a seat for the removable sampling member when said sampling member is disposed in the sampling chamber.

* * * * *